(12) United States Patent
Noshi et al.

(10) Patent No.: US 10,851,121 B2
(45) Date of Patent: Dec. 1, 2020

(54) SCALABLE POLYPROPIONATE LACTONE STEREOTETRADS

(71) Applicant: AKANOCURE PHARMACEUTICALS, INC., West Lafayette, IN (US)

(72) Inventors: Mohammad N. Noshi, West Lafayette, IN (US); Philip L. Fuchs, West Lafayette, IN (US)

(73) Assignee: AKANOCURE PHAMRACEUTICALS, INC., West Lafayette, IN (US)

( * ) Notice: Subject to any disclaimer, the term of this patent is extended or adjusted under 35 U.S.C. 154(b) by 0 days.

(21) Appl. No.: 16/467,892

(22) PCT Filed: Dec. 11, 2017

(86) PCT No.: PCT/US2017/065652
§ 371 (c)(1),
(2) Date: Jun. 7, 2019

(87) PCT Pub. No.: WO2018/107180
PCT Pub. Date: Jun. 14, 2018

(65) Prior Publication Data
US 2019/0367540 A1      Dec. 5, 2019

Related U.S. Application Data

(60) Provisional application No. 62/497,952, filed on Dec. 9, 2016.

(51) Int. Cl.
C07F 7/04          (2006.01)
C07F 7/18          (2006.01)

(52) U.S. Cl.
CPC .............. *C07F 7/1804* (2013.01); *C07F 7/04* (2013.01); *C07B 2200/13* (2013.01)

(58) Field of Classification Search
CPC .......................... C07F 7/1804; C07B 2200/13
USPC ........................................................ 549/291
See application file for complete search history.

(56) References Cited

U.S. PATENT DOCUMENTS 5,681,847 A * 10/1997 Longley ............... A61K 31/366
                                                          514/459
2004/0138485 A1    7/2004 Fuchs et al.

FOREIGN PATENT DOCUMENTS

GB         2280677 A  *  2/1995  ........... C07D 263/22
WO    WO-2016/057606       4/2016

OTHER PUBLICATIONS

Wan Pyo Hong et al. Synthesis of the C1-C20 and C15-C27 segments of Aplyronine A (Year: 2011).*
Masahiro Muyazawa et al , Streoselective Synthesis of C1-C7 segment of (+)-Discodermolide (Year: 1997).*
Cole Clissold et al. Synthesis of Tetrasubstitued delta-lactones. (Year: 1997).*
International Search Report and Written Opinion, PCT/US2017/065652, Akanocure Pharmaceuticals, Inc., 13 pages (dated Feb. 26, 2018).
Peed et al., Organic Letters, 13(14), pp. 3592-3595 (2011) for Appl. No. PCT/US2017/065652.
Pubchem CID 10891186 pp. 1-9 (2006)for Appl. No. PCT/US2017/065652.
Pubchem CID 11737786 pp. 1-9 (2006)for Appl. No. PCT/US2017/065652.
Pubchem CID 59891818 pp. 1-10 (2012)for Appl No. PCT/US2017/065652.
Pubchem CID 90864223 pp. 1-10 (2015)for Appl. No. PCT/US2017/065652.
Ahmad El-Awa et al., "Asymmetric Synthesis of All Eight Seven-Carbon Dipropionate Stereotetrads", Journal of the American Chemical Society, vol. 129, No. 29, Jul. 1, 2007 (Jul. 1, 2007), pp. 9086-9093, XP055703452, ISSN: 0002-7863, DOI: 10.1021/ja071217x.
Ahmad El-Awa et al., "Double Lawton SN 2'Addition to Epoxyvinyl Sulfones:? Selective Construction of the Stereotetrads of Aplyronine A", Organic Letters, vol. 8, No. 14, Jul. 1, 2006 (Jul. 1, 2006), pp. 2905-2908, XP055705909, ISSN: 1523-7060, DOI: 10.1021/010605301.
Armando Cordova et al., "Amino Acid Catalyzed Neogenesis of Carbohydrates: A Plausible Ancient Transformation", Chemistry—A European Journal, vol. 11, No. 16, Aug. 5, 2005 (Aug. 5, 2005), pp. 4772-4784, . XP055705910, ISSN: 0947-6539, DOI: 10.1002/chem.200500139.
Christophe Roche et al., "A Ruthenium-Mediated Asymmetric Hydrogenation Approach to the Synthesis of Discodermolide Subunits", SYNLETT,vol. 2009, No. 04, Feb. 16, 2009 (Feb. 16, 2009), pp. 573-576, XP055705907, ISSN: 0936-5214, DOI: 10.1055/s-0028-1087917.

(Continued)

*Primary Examiner* — Rita J Desai
(74) *Attorney, Agent, or Firm* — Foley & Lardner LLP

(57) ABSTRACT

The present technology is directed to polypropionate lactone stereotetrads of Formula (I) (or a pharmaceutically acceptable salt and/or solvate thereof) which are significant intermediates for multiple synthetic applications.

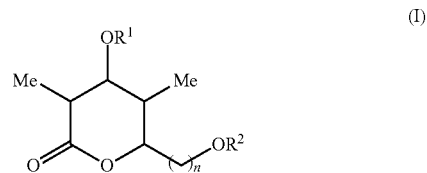

(I)

9 Claims, 2 Drawing Sheets

(56) References Cited

OTHER PUBLICATIONS

Clissold C et al., "Synthesis of Tetrasubstituted A2-Lactones", Tetrahedron Letters, Elsevier LTD, Amsterdam, NL, vol. 38, No. 46, Nov. 17, 1997 (Nov. 17, 1997), pp. 8105-8108, XP026952908, ISSN: 0040-4039 [retrieved on Nov. 17, 1997].
Florence Eustache et al., "Synthesis of the C14-C25 Subunit of Bafilomycin A 1", Journal of Organic Chemistry, vol. 68, No. 26, Dec. 1, 2003 (Dec. 1, 2003), pp. 9994-10002, XP055704559, ISSN: 0022-3263, DOI: 10.1021/jo035068m.
Extended European Search Report, App. No. EP 17879211.5 (dated Jun. 26, 2020).
Ian Paterson et al., "Development of a Third-Generation Total Synthesis of ( )-Discodermolide: An Expedient Still-Gennari-Type Fragment Coupling Utilizing an Advanced [beta]-Ketophosphonate", Journal of Organic Chemistry, vol. 70, No. 14, Jul. 1, 2005 (Jul. 1, 2005), pp. 5494-5507, XP055705915, ISSN: 0022-3263, DOI: 10.1021/jo050481a.
J. Yadav et al., "A Stereoselective Synthesis of the C20-C32 Fragment of the Phorboxazoles", SYNLETT, vol. 2007, No. 10, Jun. 1, 2007 (Jun. 1, 2007), pp. 1577-1580, XP055705908, ISSN: 0936-5214, DOI: 10.1055/s-2007-982556.
Jeong et al., "Stereoselective Synthesis of Pamamycin-607", Journal of the American Chemical Society,vol. 124, No. 49, Dec. 1, 2002 (Dec. 1, 2002), pp. 14655-14662, XP055705949, ISSN: 0002-7863, DOI: 10.1021/ja0279646.
Jun'ichi Uenishi et al., "Stereoselective Synthesis of Fully Substituted d-Lactone; the C1-C8 Fragment of Discodermolide", Heterocycles, vol. 59, No. 1, Jan. 1, 2003 (Jan. 1, 2003), pp. 347-358, XP055704557, ISSN: 0385-5414, DOI: 10.3987/COM-02-S46.
Luiz C Dias et al., "Issue in Honor of Prof. Eusebio Juaristi ARKIVOC 2005 (vi) 62-87 Total synthesis of the potent immunosuppressant (-)? Pironetin Dedicated to Professor Eusebio Juaristi on the occasion of his 55 th birthday", Apr. 19, 2005 (Apr. 19, 2005), XP055705934,Retrieved from the Internet: URL:https://quod.lib.umich.edu/cache// 5/5/5/5550190.0006.607/5550190.0006.607.pdf#page=1;zoom=75 [retrieved on Jun. 17, 2020].
Luiz C. Dias et al., "Total Synthesis of (-)-Pironetin", Organic Letters, vol. 5, No. 3, Feb. 1, 2003 (Feb. 1, 2003), pp. 265-268, XP055705948, ISSN: 1523-7060, DOI: 10.1021/ol027211o.
Masahiro., "stereoselective synthesis of the C1-C7 segment of( )? Discodermolide", Dec. 1, 1997 (Dec. 1, 1997), XP055705962, Retrieved from the Internet: URL:https://www.journal.csj.jp/doi/pdf/10.1246/cl.1997.1191 [retrieved on Jun. 17, 2020].
P. Veeraraghavan Ramachandran et al., "Diastereoselective Dihydroxylation and Regioselective Deoxygenation of Dihydropyranones:? A Novel Protocol for the Stereoselective Synthesis of C 1-C 8 and C 15-C 21 Subunits of ( )-Discodermolide", The Journal of Organic Chemistry, vol. 69, No. 19, Sep. 1, 2004 (Sep. 1, 2004), pp. 6294-6304, XP055037033, ISSN: 0022-3263, DOI: 10.1021/jo0492416.
Yadav JS et al., "Towards the synthesis of ( )-discodermolide", Tetrahedron Letters, Elsevier LTD, Amsterdam, NL, vol. 42, No. 28, Jul. 9, 2001 (Jul. 9, 2001), pp. 4713-4716, XP004245785, ISSN: 0040-4039, DOI: 10.1016/S0040-4039(01)00799-7.
Yuzhong Chen et al., "Synthesis of Termini-Differentiated 6-Carbon Stereotetrads:? An Alkylative Oxidation Strategy for Preparation of the C21-C26 Segment of Apoptolidin 1", Organic Letters,vol. 4, No. 21, Oct. 1, 2002 (Oct. 1, 2002), pp. 3571-3574, XP055704560, ISSN: 1523-7060, DOI: 10.1021/ol026377m.

\* cited by examiner

SCALABLE POLYPROPIONATE LACTONE STEREOTETRADS

CROSS-REFERENCE TO RELATED APPLICATIONS

This application is a National Stage Application of PCT/US2017/065652, filed Dec. 11, 2017, which claims priority to U.S. Provisional Application No. 62/497,952, filed Dec. 9, 2016, the contents of each of which are incorporated herein by reference in their entirety for any and all purposes.

FIELD

The present technology is directed to polypropionate lactone stereotetrads as valuable tools for multiple synthetic applications.

SUMMARY

In an aspect, a compound according to Formula I is provided

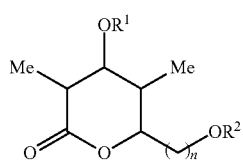

(I)

or a pharmaceutically acceptable salt and/or solvate thereof, wherein
$R^1$ is H, trimethylsilyl, triethylsilyl, tert-butyl-dimethylsilyl, triisopropylsilyl, tert-butyl-diphenylsilyl, triphenylsilyl, dimethylphenylsilyl, methyldiphenylsilyl, acetyl, pivaloyl, trichloroacetyl, 2,2,2-trichloroethoxycarbonyl, benzyl, p-methoxybenzyl, 3-(phenyl sulfonyl)propionyl, tosyl, or mesyl;
$R^2$ is H, trimethylsilyl, triethylsilyl, tert-butyl-dimethylsilyl, triisopropylsilyl, tert-butyl-diphenylsilyl, triphenylsilyl, dimethylphenylsilyl, methyldiphenylsilyl, acetyl, pivaloyl, trichloroacetyl, 2,2,2-trichloroethoxycarbonyl, benzyl, p-methoxybenzyl, 3-(phenylsulfonyl)propionyl, tosyl, or mesyl; and
n is 1 or 2;
provided that the compound of Formula I is not:

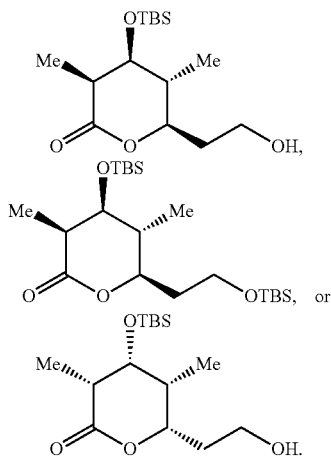

DETAILED DESCRIPTION

Figure 1:
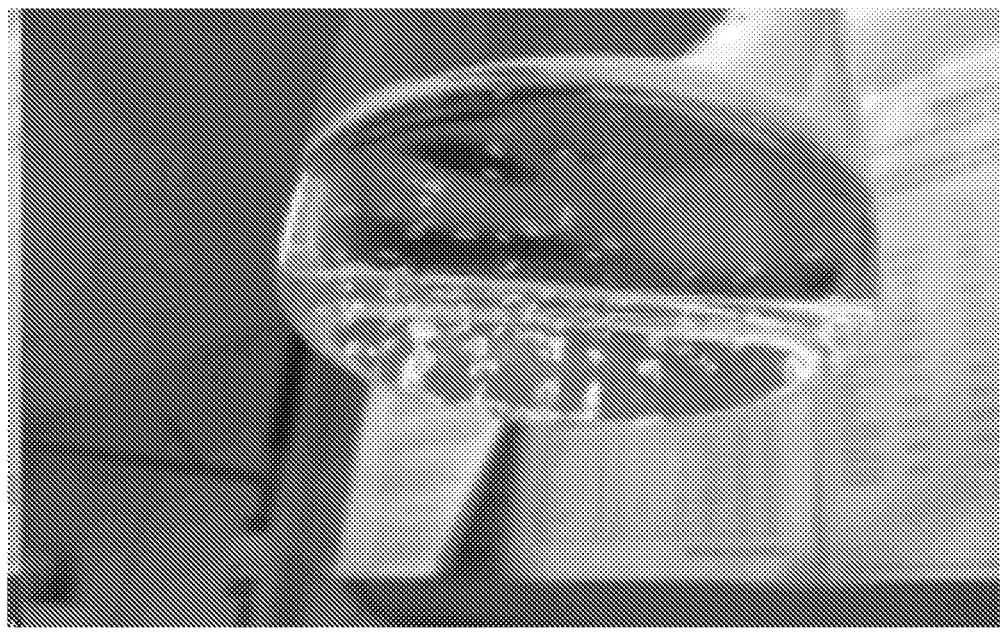
FIG. 1 provides a photograph of crystals of an embodiment of the present technology, according to the working examples.

The following terms are used throughout as defined below.

As used herein and in the appended claims, singular articles such as "a" and "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

The terms "pivaloyl", "tosyl", and "mesyl" will be understood by persons of ordinary skill in the art. However, to the extent one or more of such terms are not clear to persons of ordinary skill in the art, the term "pivaloyl" refers to $(CH_3)_3CC(O)$—, the term "tosyl" refers to

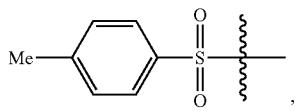

and the term "mesyl" refers to

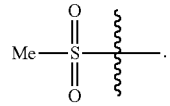

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 atoms refers to groups having 1, 2, or 3 atoms. Similarly, a group having 1-5 atoms refers to groups having 1, 2, 3, 4, or 5 atoms, and so forth.

Pharmaceutically acceptable salts of compounds described herein are within the scope of the present technology and include acid or base addition salts which retain the desired pharmacological activity and is not biologically undesirable (e.g., the salt is not unduly toxic, allergenic, or irritating, and is bioavailable). When the compound of the present technology has a basic group, such as, for example, an amino group, pharmaceutically acceptable salts can be formed with inorganic acids (such as hydrochloric acid, hydroboric acid, nitric acid, sulfuric acid, and phosphoric acid), organic acids (e.g., alginate, formic acid, acetic acid, benzoic acid, gluconic acid, fumaric acid, oxalic acid, tartaric acid, lactic acid, maleic acid, citric acid, succinic acid, malic acid, methanesulfonic acid, benzenesulfonic acid, naphthalene sulfonic acid, and p-toluenesulfonic acid) or acidic amino acids (such as aspartic acid and glutamic acid). When the compound of the present technology has an acidic group, such as for example, a carboxylic acid group, it can form salts with metals, such as alkali and earth alkali metals (e.g., $Na^+$, $Li^+$, $K^+$, $Ca^{2+}$, $Mg^{2+}$, $Zn^{2+}$) ammonia or organic amines (e.g., dicyclohexylamine, trimethylamine, triethylamine, pyridine, picoline, ethanolamine, diethanolamine, triethanolamine) or basic amino acids (e.g., arginine, lysine and ornithine). Such salts can be prepared in situ during isolation and purification of the compounds or by separately reacting the purified compound in its free base or free acid form with a suitable acid or base, respectively, and isolating the salt thus formed.

Those of skill in the art will appreciate that compounds of the present technology may exhibit the phenomena of tautomerism, conformational isomerism, geometric isomerism and/or stereoisomerism. As the formula drawings within the specification and claims can represent only one of the possible tautomeric, conformational isomeric, stereochemical or geometric isomeric forms, it should be understood that the present technology encompasses any tautomeric, conformational isomeric, stereochemical and/or geometric isomeric forms of the compounds having one or more of the utilities described herein, as well as mixtures of these various different forms.

"Tautomers" refers to isomeric forms of a compound that are in equilibrium with each other. The presence and concentrations of the isomeric forms will depend on the environment the compound is found in and may be different depending upon, for example, whether the compound is a solid or is in an organic or aqueous solution. For example, in aqueous solution, quinazolinones may exhibit the following isomeric forms, which are referred to as tautomers of each other:

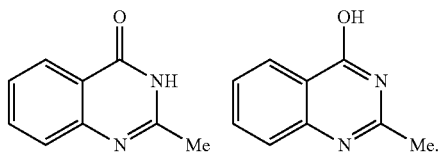

As another example, guanidines may exhibit the following isomeric forms in protic organic solution, also referred to as tautomers of each other:

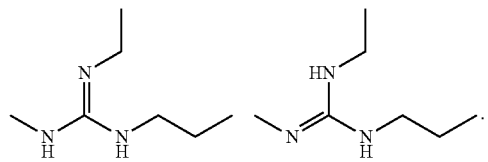

Because of the limits of representing compounds by structural formulas, it is to be understood that all chemical formulas of the compounds described herein represent all tautomeric forms of compounds and are within the scope of the present technology.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The compounds of the present technology may exist as solvates, especially hydrates. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates among others. The identification and preparation of any particular solvate is within the skill of the ordinary artisan of synthetic organic or medicinal chemistry.

The Present Technology

The historic synthesis of the "Corey lactones" (see Scheme 1; Corey, E. J.; Weinshenker, N. M.; Schaaf, T. K.; Huber, W. *J. Am. Chem. Soc.* 1969, 91, 5675) bearing contiguous stereocenters has powerfully enabled the enantioselective total synthesis of multiple prostaglandins, a family of exceptionally bioactive molecules with hormone-like effects in animals and humans. Since Corey revealed his chiral lactones in 1969, and with the continuous discovery of novel bioactive natural products, there exists an unsatisfied need for powerful synthetic tools that can enable synthesis of such natural products on practical scales.

Scheme 1.

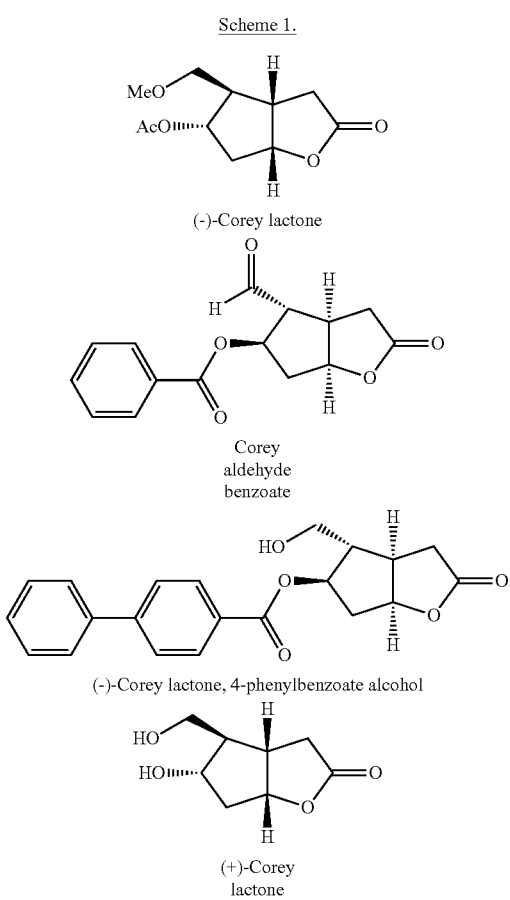

(-)-Corey lactone

Corey aldehyde benzoate (-)-Corey lactone, 4-phenylbenzoate alcohol (+)-Corey lactone Over 10,000 polyketide natural products have been discovered to date where 1% of this number possesses desired biological activity. Nevertheless, this seemingly small fraction constitutes more than five times the number from any other family of natural products thereby positioning polyketides as the ideal starting point for drug discovery.

A key feature of polyketide natural products is the existence of complex stereodefined arrays of contiguous stereocenters of alternating methyl and hydroxyl groups known as "polypropionates". In many instances, the number of contiguous stereocenters is four thus creating a "stereotetrad". The synthetic obstacles of elaborating such stereotetrads in a selective and enantiopure manner as well as provide a synthetic route with the flexibility and robustness to manufacture these complex arrays on practical scale is a significant challenge.

The present technology is directed towards polypropionate lactone stereotetrads as valuable tools for many synthetic applications. These applications include but not limited to processes such as lactone openings to termini-differentiated linear fragments, selective protections, selective deprotections, reductions to aldehydes, reductions to lactols, olefination processes leading to cis and/or trans olefins, olefination processes leading to E and/or Z-olefins, reductions to alcohols, subsequent functionalization of primary alcohols including but not limited to iodinations, tosylations, organometallic formations, and subsequent couplings that involve carbon-carbon bond formations. For example, the polypropionate lactone stereotetrads of the present technology may be utilized in the synthesis of Apyronine A as well as analogues thereof, as illustrated in Hong, W. P. et al. "Synthesis of the C1-C20 and C15-C27 Segments of Aplyronine A" *Org. Lett.*, 2011, 13(24), 6342-6345, incorporated herein by reference.

Thus, in an aspect, a compound according to Formula I is provided

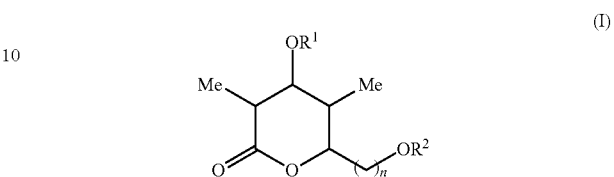

or a pharmaceutically acceptable salt and/or solvate thereof, wherein $R^1$ is H, trimethylsilyl (TMS), triethylsilyl (TES), tert-butyl-dimethylsilyl (TBS), triisopropylsilyl (TIPS), tert-butyl-diphenylsilyl (TBDPS), triphenylsilyl, dimethylphenylsilyl, methyldiphenylsilyl, acetyl (Ac), pivaloyl (Piv), trichloroacetyl, 2,2,2-trichloroethoxycarbonyl (Troc), benzyl, p-methoxybenzyl (PMB), 3-(phenylsulfonyl)propionyl, tosyl (Ts), or mesyl (Ms);

$R^2$ is H, TMS, TES, TBS, TIPS, TBDPS, triphenylsilyl, dimethylphenylsilyl, methyldiphenylsilyl, Ac, Piv, trichloroacetyl, Troc, benzyl, PMB, 3-(phenylsulfonyl)propionyl, Ts, or Ms; and n is 1 or 2;

provided that the compound of Formula I is not:

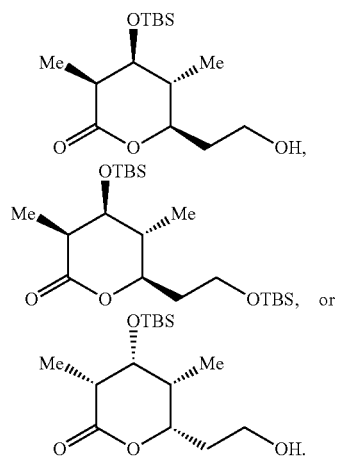

In any embodiment herein, it may be that the compound of Formula I is not:

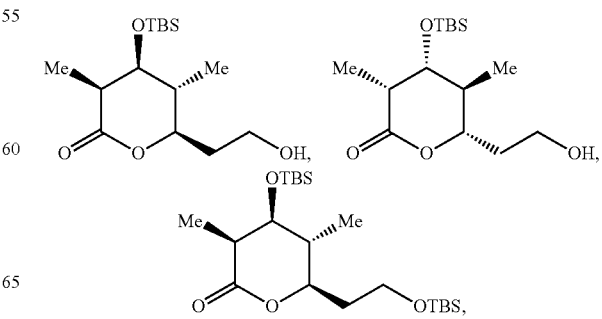

-continued
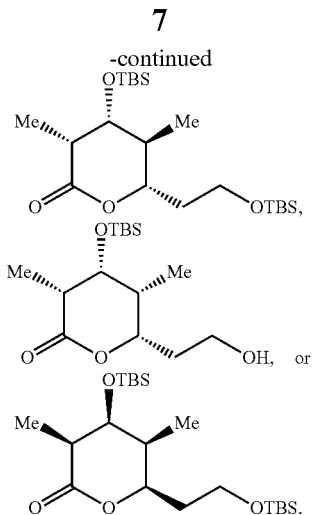
The compound of Formula I may be a compound of any one of Formulas $I_1$-$I_{16}$:
(I₁)
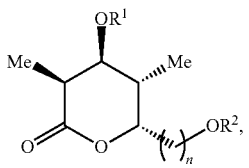
(I₂)
(I₃)
(I₄)
(I₅)
(I₆)
(I₇)
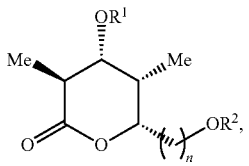
(I₈)
(I₉)
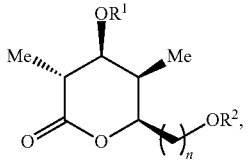
(I₁₀)
(I₁₁)
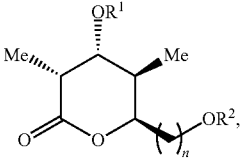
(I₁₂)
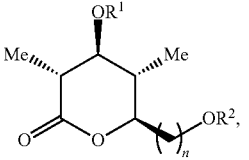
(I₁₃)
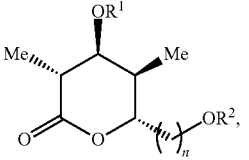
(I₁₄)
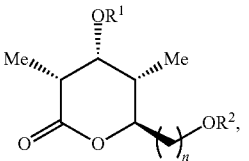
(I₁₅)
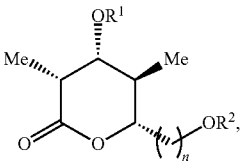

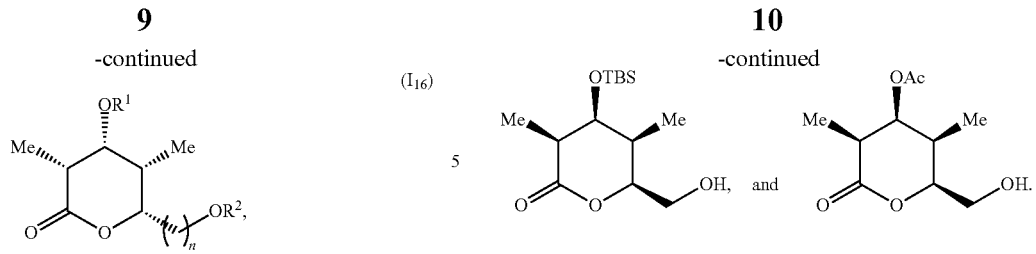

where $R^1$, $R^2$, and n are defined regarding Formula I.

In any embodiment herein, it may be that $R^1$ is TBS or acetyl. In any embodiment herein, it may be that $R^2$ is triphenylsilyl. It may be that the compound of Formula I is a crystalline solid. As crystalline solids, this enables facile packaging, shipping, and weighing of such compounds. In addition, compounds where $R^1$ and/or $R^2$ include aromatic groups, e.g., triphenylsilyl, are UV-active, allowing for facile monitoring of reactions involving such compounds without the need for staining techniques. Exemplary compounds of Formula I include, but are not limited to:

The examples herein are provided to illustrate advantages of the present technology and to further assist a person of ordinary skill in the art with preparing or using the compounds of the present technology. The examples herein are also presented in order to more fully illustrate the preferred aspects of the present technology. The examples should in no way be construed as limiting the scope of the present technology, as defined by the appended claims. The examples can include or incorporate any of the variations, aspects or aspects of the present technology described above. The variations, aspects or aspects described above may also further each include or incorporate the variations of any or all other variations, aspects or aspects of the present technology.

Examples

Representative Synthetic Procedures

In addition to the procedures described in Hong, W. P. et al. "Synthesis of the C1-C20 and C15-C27 Segments of Aplyronine A" *Org. Lett.*, 2011, 13(24), 6342-6345, various representative synthetic procedures are illustrated below in Schemes 2-17.

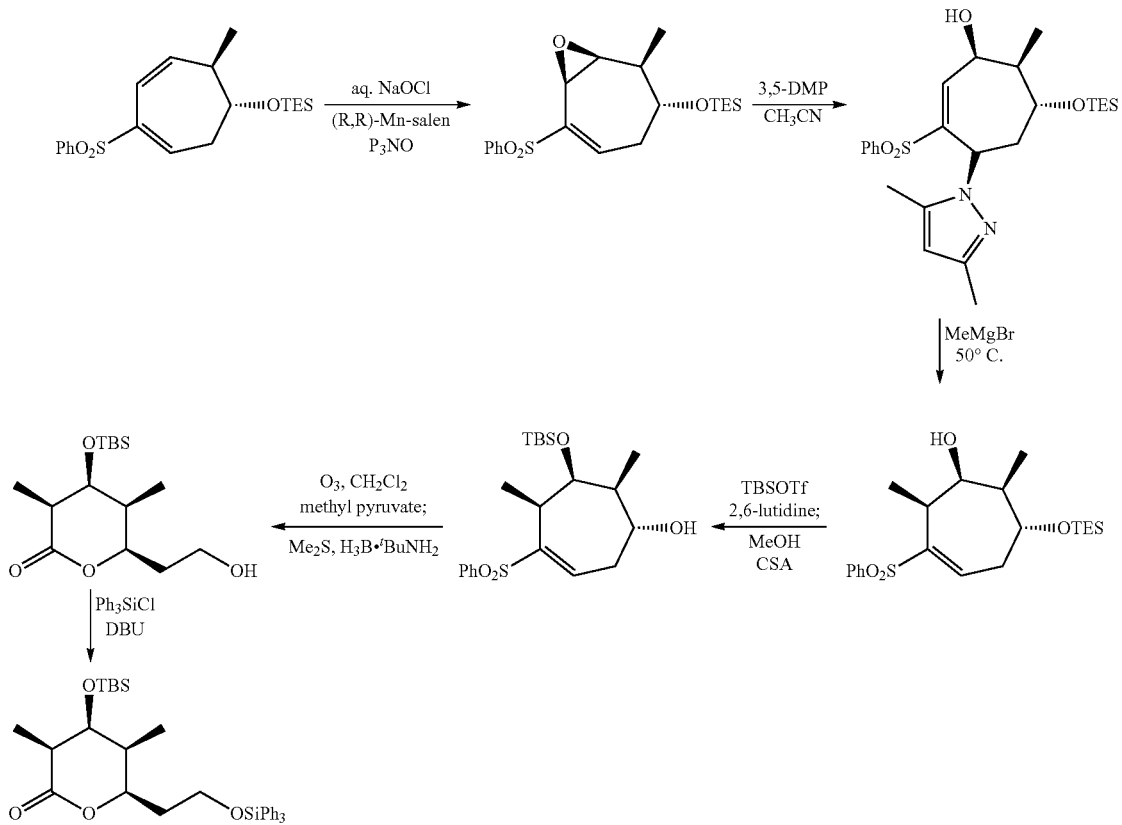

Scheme 3.
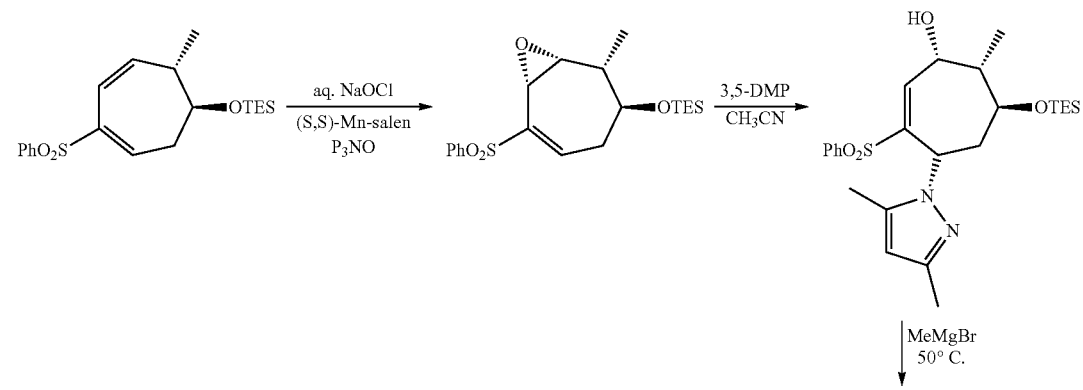
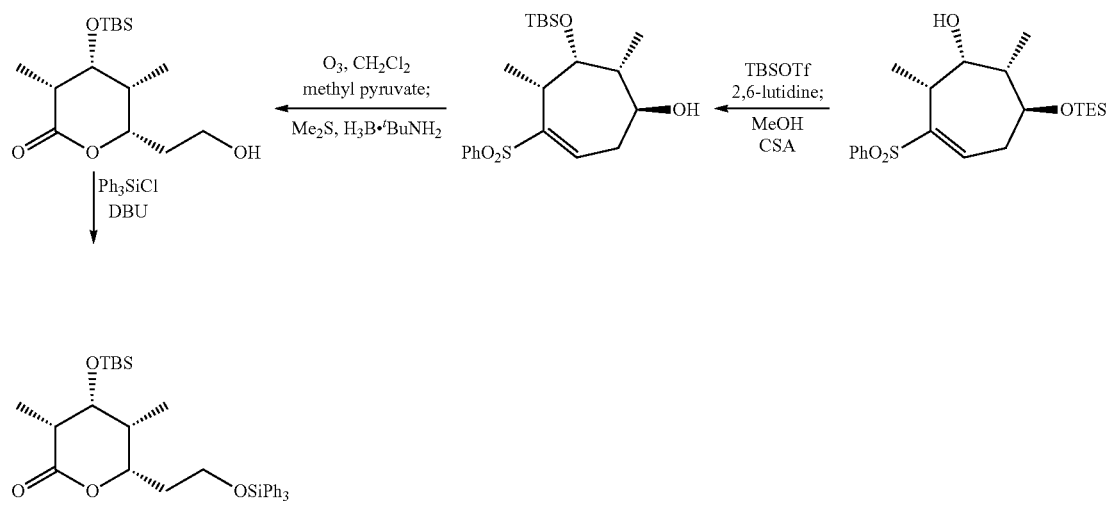
Scheme 4.
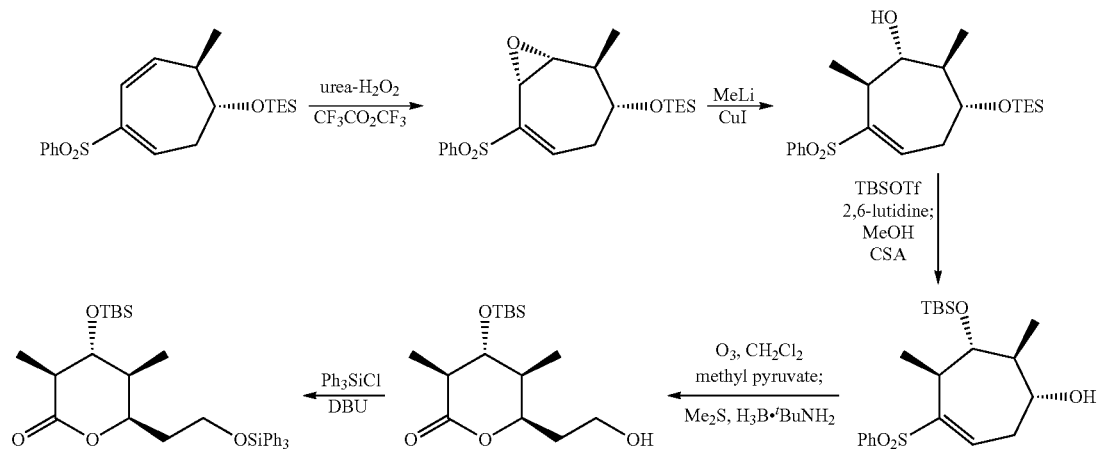

Scheme 5.
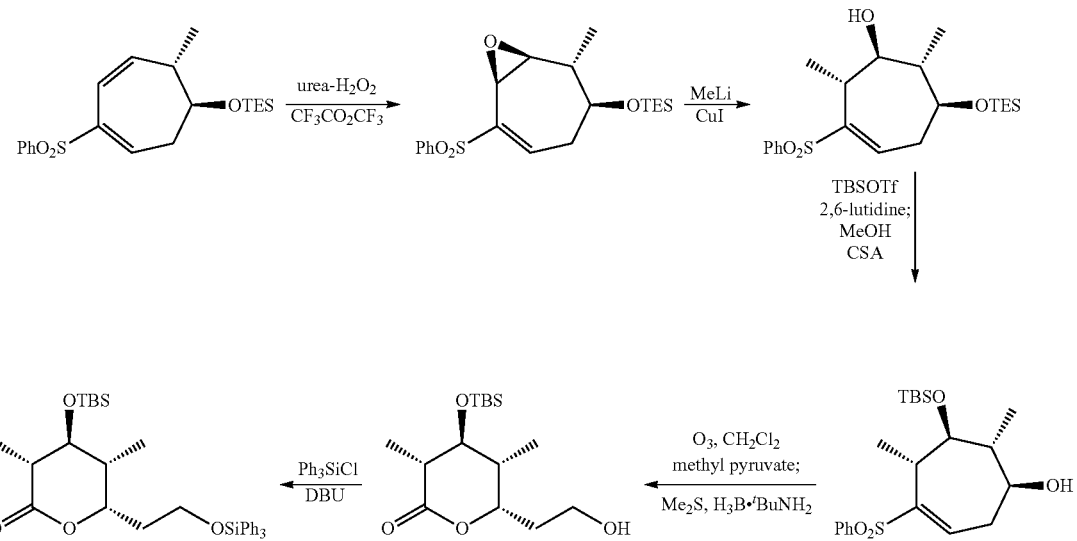
Scheme 6.
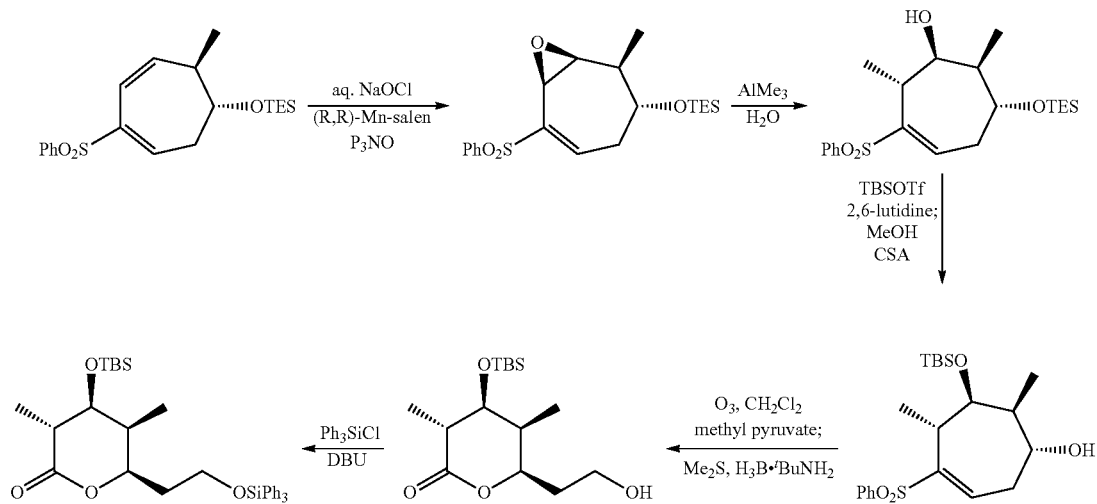
Scheme 7.
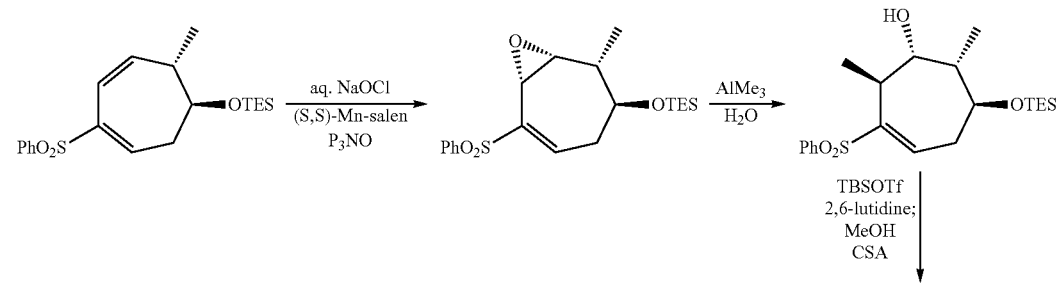

15
16
-continued
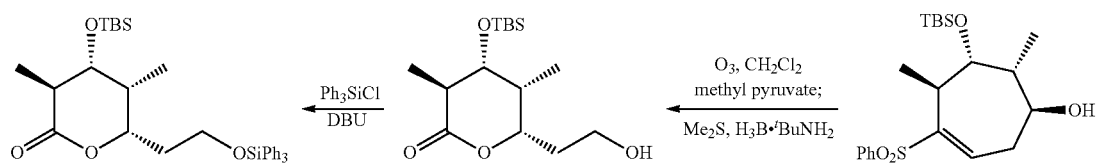
Scheme 8.
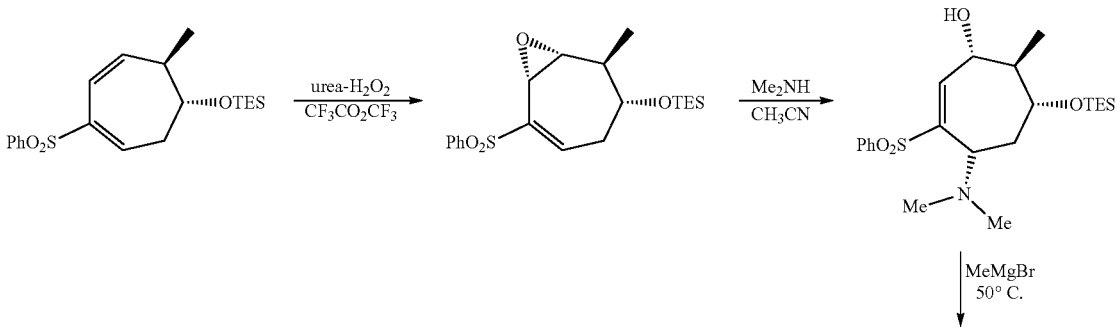
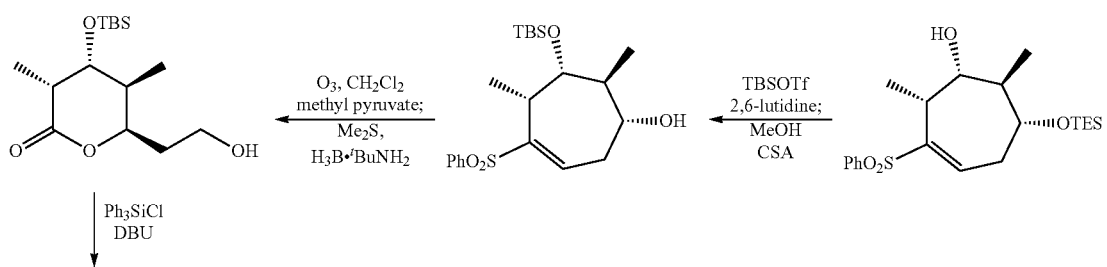
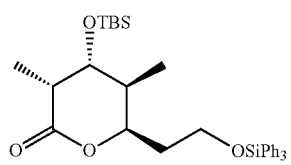
Scheme 9.
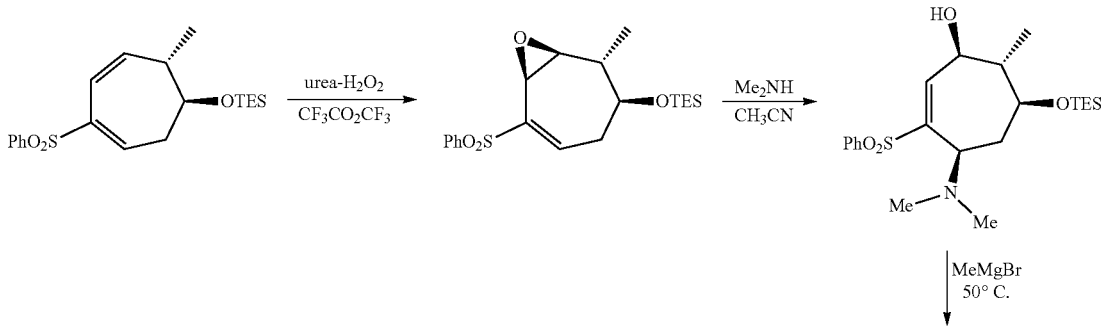

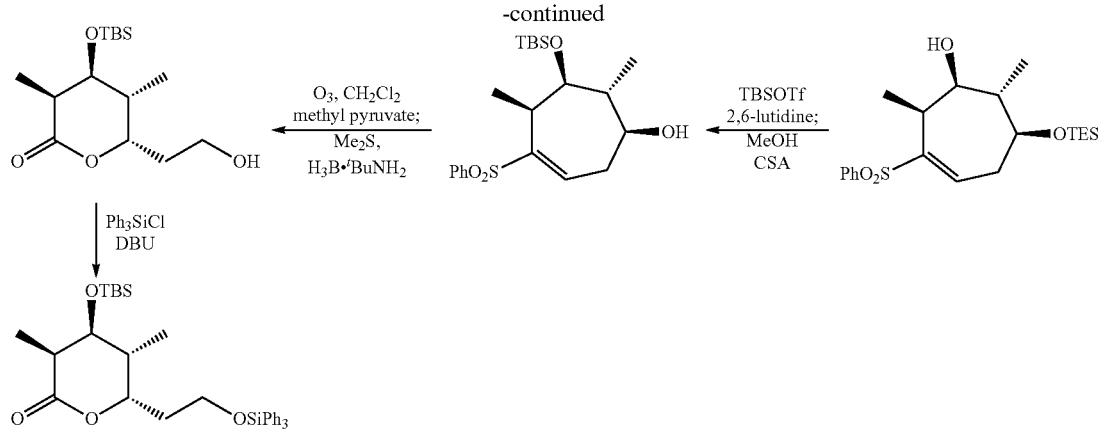
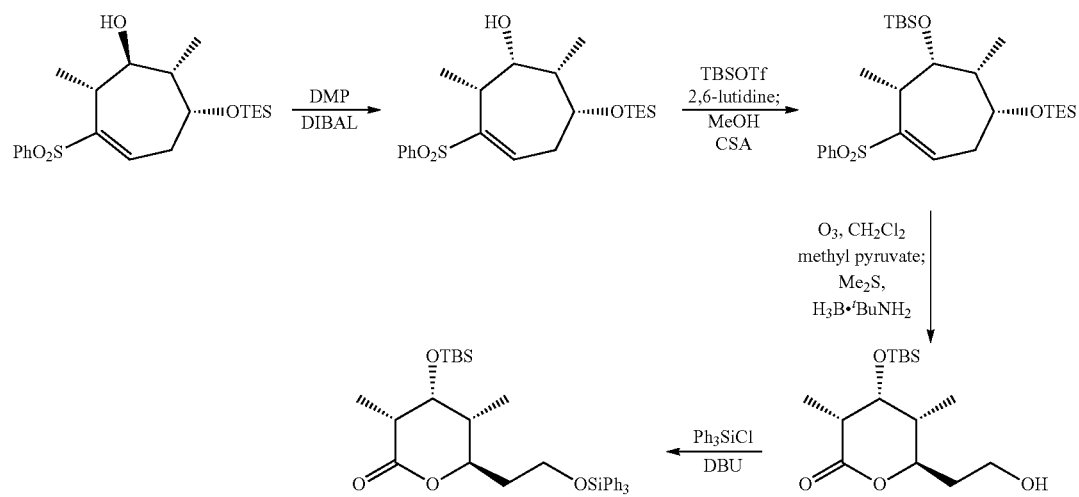
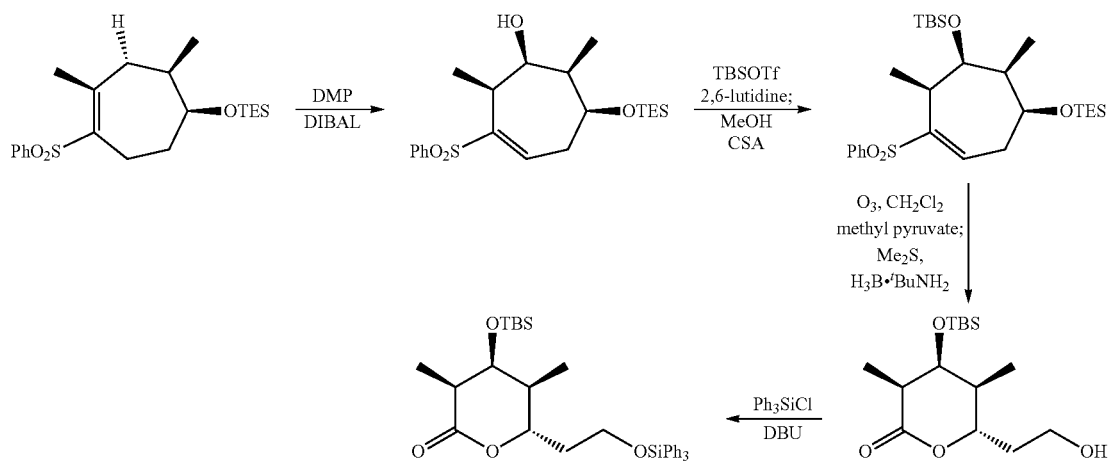

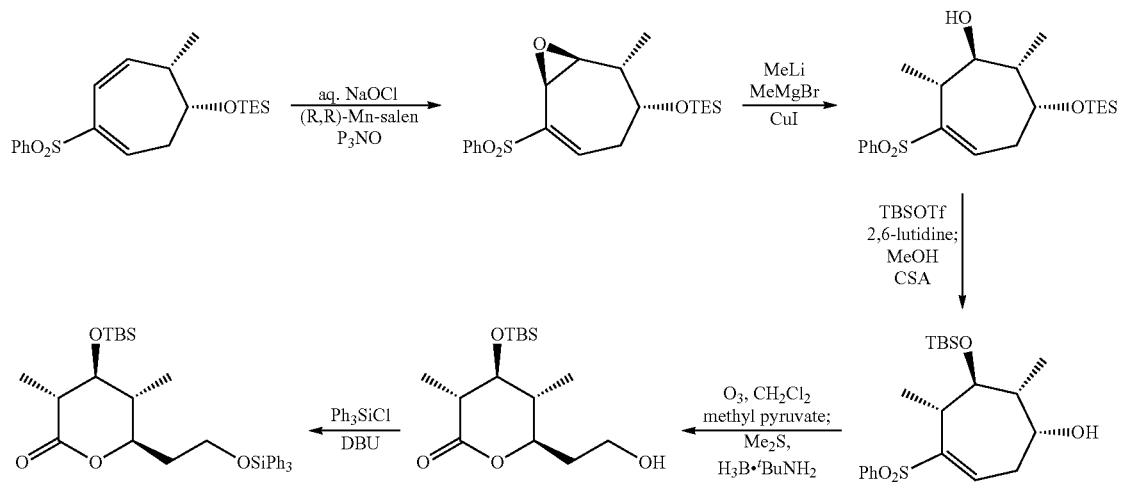
Scheme 12.
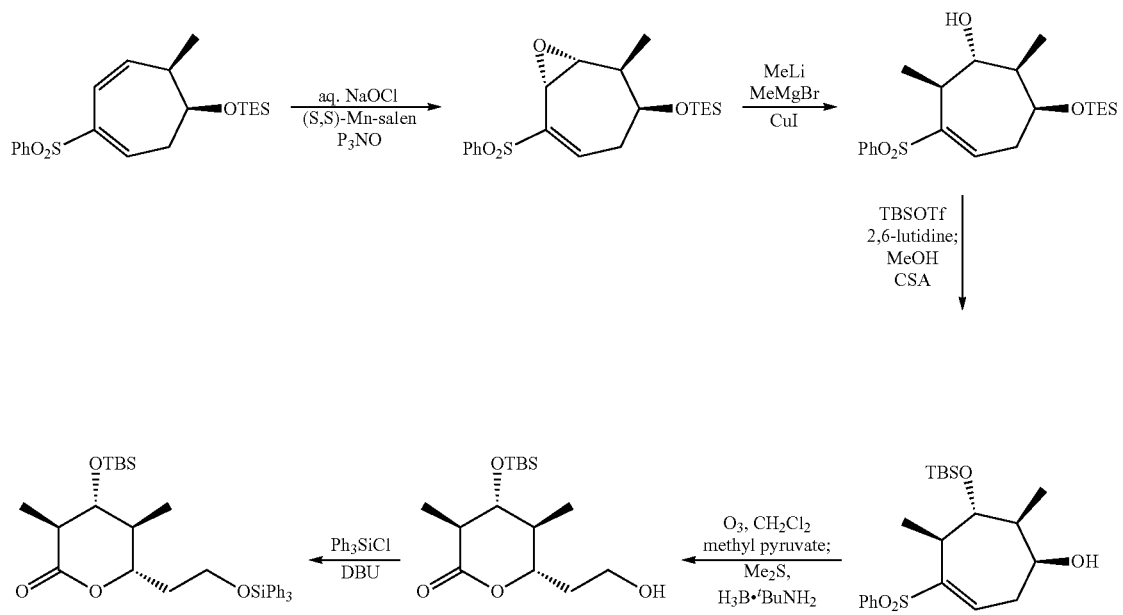
Scheme 13.
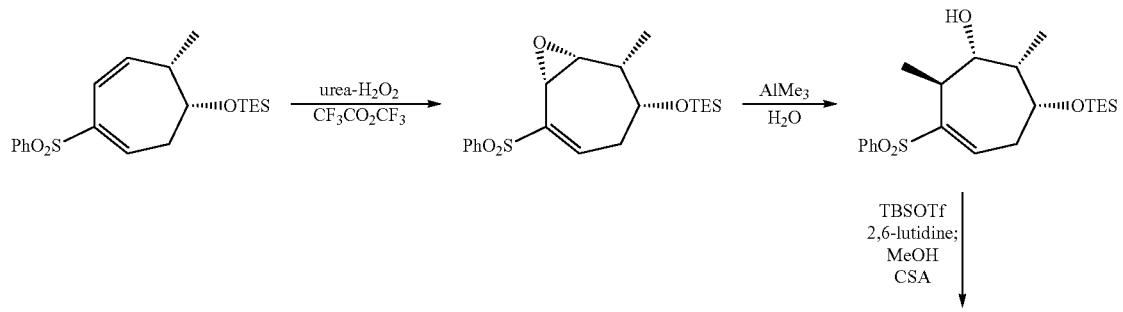
Scheme 14.

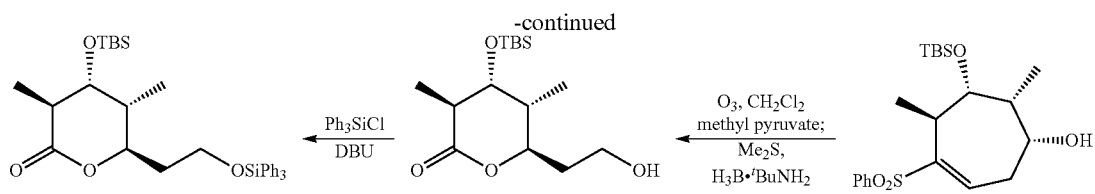
Scheme 15.
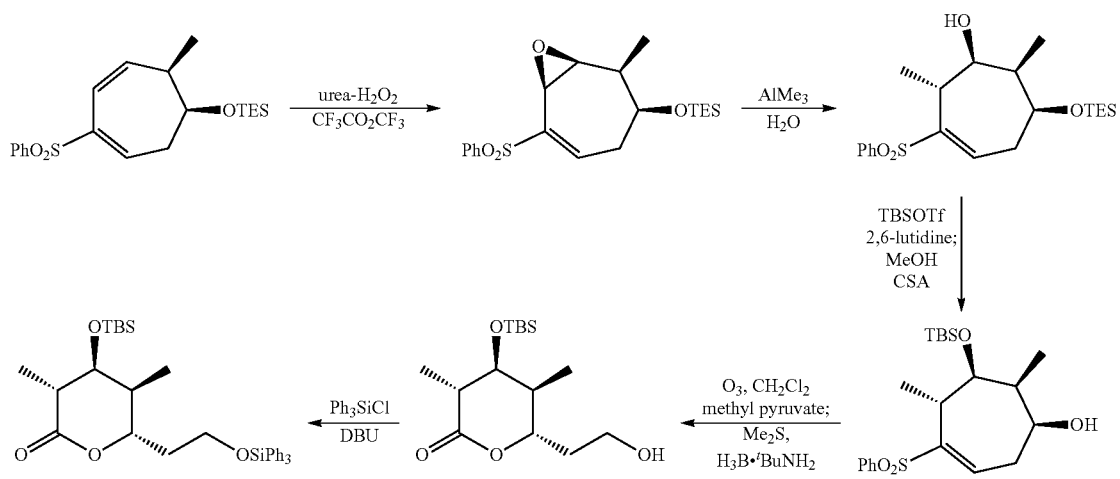
Scheme 16.
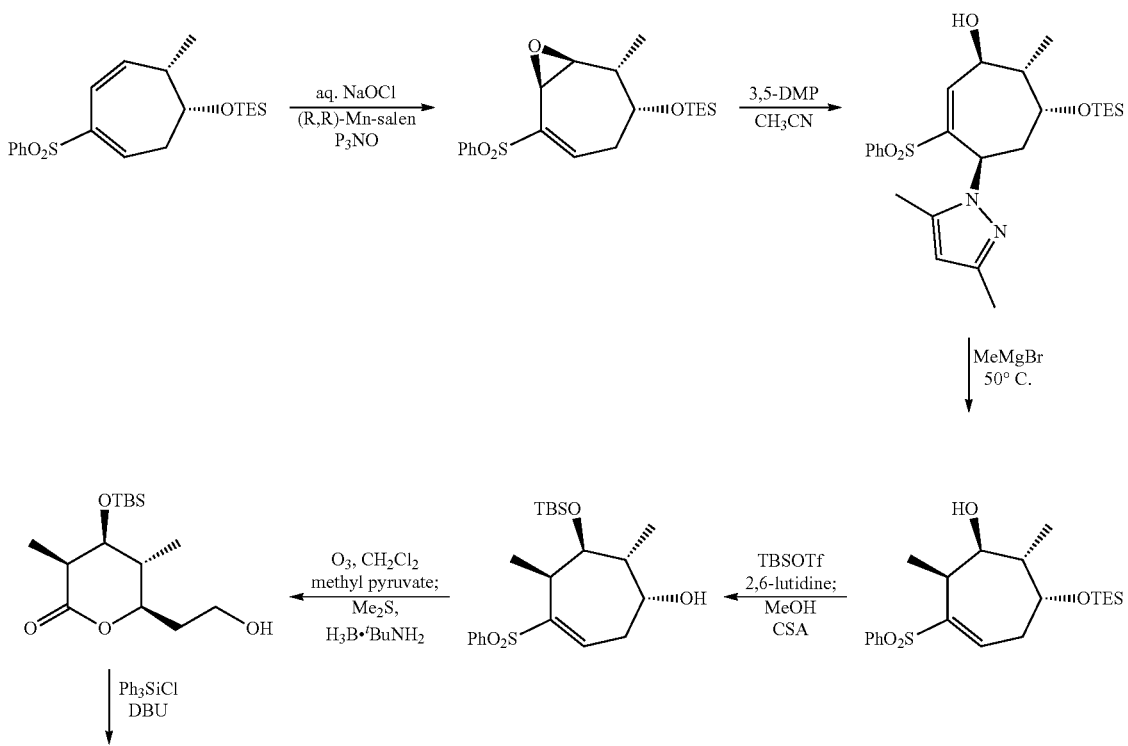

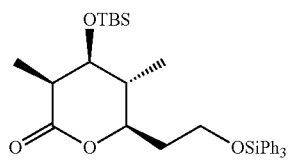

-continued

Scheme 17.

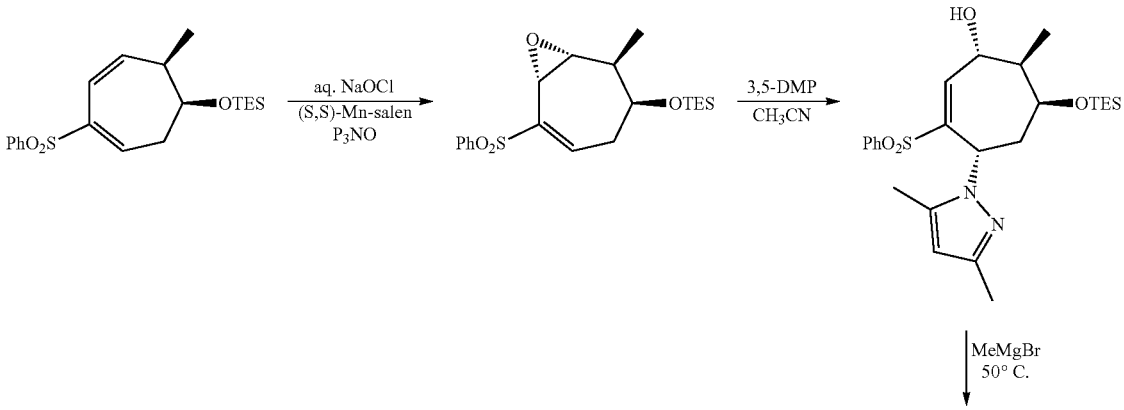

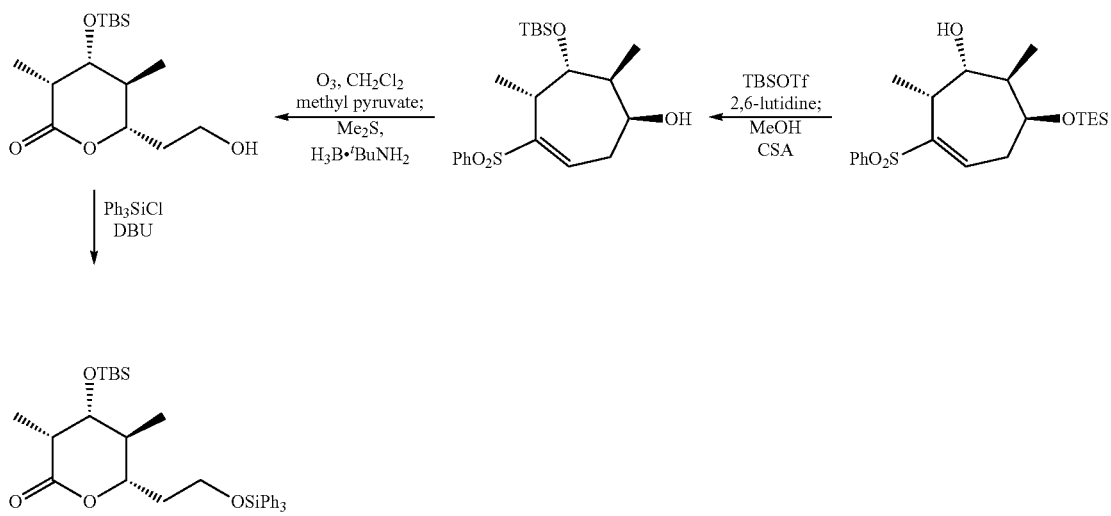

Exemplary Syntheses of Certain Compounds of Present Technology

General Synthetic and Analytical Details:

All chemical reagents and dry solvents were purchased from commercial suppliers and used without further purification. Unless otherwise indicated, reactions were performed in dried standard glassware and under an atmosphere of argon. $^1$H was recorded a 300 MHz spectrometer using tetramethyl silane as an internal standard. Chemical shifts (δ) are reported in ppm and coupling constants (J) are reported in Hz.

Example 1. Exemplary Crystalline Compound of the Present Technology

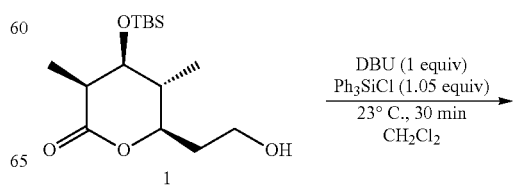

-continued

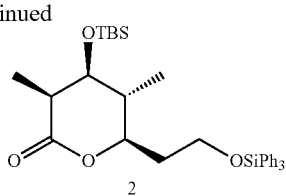

To a 50 mL round bottom flask was charged alcohol 1 (1.25 g, 4.14 mmol, 1 equiv), Ph$_3$SiCl (1.336 g, 4.35 mmol, 1.05 equiv) and dry dichloromethane (10 mL) under strict anhydrous conditions to give a clear and colorless solution. The solution was stirred at 23° C. for 5 minutes, then 1,8-diazabicyclo[5.4.0]undec-7-ene ("DBU"; 625 mL, 4.14 mmol, 1 equiv) was added dropwise, and the resulting suspension was stirred for 30-60 minutes. The reaction was diluted with hexane (10 mL), filtered through a pad of Celite®, and the filtrate was concentrated under vacuum to give a crude yellow oil. Crystallization from hexane-dichloromethane afforded 2 as white prisms (3.8 g, 92%). $^1$H NMR (300 MHz, CDCl$_3$) δ 7.62-7.57 (m, 6H), 7.46-7.33 (m, 9H), 4.13-3.92 (m, 2H), 3.87 (dt, J=3.0, 15.0 Hz, 1H), 3.62-3.58 (m, 1H), 2.36 (ddd, J=3.0, 9.0, 15.0 Hz, 1H), 2.02-1.87 (m, 1H), 1.84-1.67 (m, 2H), 1.15 (d, J=6.0 Hz, 3H), 0.94 (d, J=6.0 Hz, 3H), 0.83 (s, 9H), 0.01 (s, 6H). FIG. 1 provides a photograph of crystals of 2 during crystallization.

Example 2. Exemplary One-Pot Elaboration of a Compound of the Present Technology

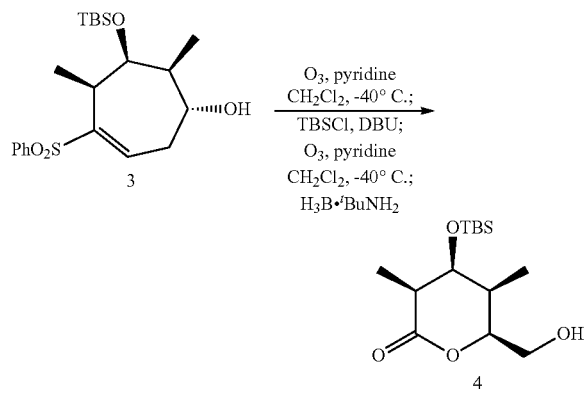

A 100 mL dry 3-neck flask was fit with a gas inlet adapter attached to a gas dispersion tube, a drying tube, and an outlet to an aqueous 10% potassium iodide solution. The flask was charged with 3 (5.0 g, 12.18 mmol, 1 equiv), pyridine (4.9 mL, 60.9 mmol, 5.0 equiv), and dry dichloromethane (60 mL). The resulting solution was cooled to −40° C., ozone was bubbled for 60 minutes, then purged with argon for 30 minutes. The solution was concentrated under vacuum, after which the resulting oil was dissolved in dichloromethane (30 mL). To this mixture TBSCl (5.67 g, 36.54 mmol, 3.0 equiv) was added followed by DBU (5.5 mL, 36.54 mmol, 3.0 equiv). After 30 minutes, the yellow solution was cooled to −40° C., pyridine (4.9 mL, 60.9 mmol, 5.0 equiv) was added, and ozone was bubbled for 60 minutes, then purged with argon for 30 minutes. After cooling for 30 minutes at 5° C., H$_3$B·$^t$BuNH$_2$ (1.59 g, 18.27 mmol, 1.5 equiv) was added, and stirring was continued for 30 minutes. The organic phase was washed with 5% aqueous HCl (30 mL), saturated aqueous NaHCO$_3$ (30 mL), dried with brine (30 mL), then with anhydrous sodium sulfate. The organic phase was filtered and concentrated under vacuum to give a crude brownish oil. Purification over a short silica pad afforded alcohol 4 as a pale yellow oil. (2.42 g, 69%). $^1$H NMR (300 MHz, CDCl$_3$) δ 4.83 (dt, J=3.0, 6.0 Hz, 1H), 4.16 (dd, J=5.4, 5.4 Hz, 1H), 2.87 (dd, J=8.9, 16.5 Hz, 1H), 2.77-2.69 (m, 1H), 2.63 (dd, J=4.8, 16.3 Hz, 1H), 2.35-2.27 (m, 1H), 1.22 (d, J=7.2 Hz, 3H), 0.96 (d, J=7.2 Hz, 3H), 0.89 (s, 9H), 0.06 (s, 3H), 0.06 (s, 3H).

Example 3. Exemplary Selective and Facile Deprotection of a Primary Triphenylsilyl Group in the Presence of a Secondary Tert-Butyldimethylsilyl Group

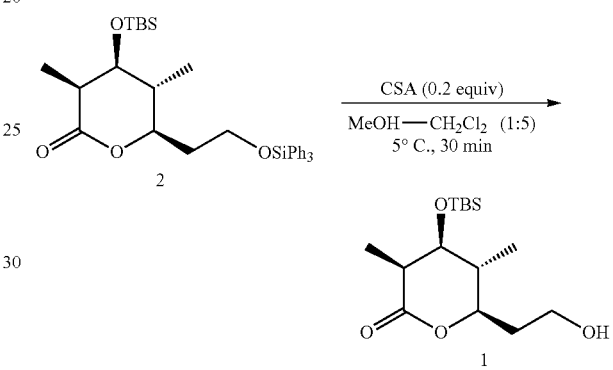

A 50 mL flask was charged with 2 (560 mg, 1 mmol, 1 equiv), methanol (2.0 mL), dichloromethane (10.0 mL), and the solution was cooled at 5° C. for 30 minutes. (+)-Camphorsulfonic acid (47.4 mg, 0.2 mmol, 0.2 equiv) was added portionwise, and the solution was stirred for 30 minutes. The reaction mixture was diluted with dichloromethane (20 mL), washed with saturated aqueous NaHCO$_3$ (20 mL), dried with brine (20 mL), then with anhydrous sodium sulfate. Filtration followed by concentration under vacuum gave crude yellow oil. Purification by filtration over a short silica pad afforded 1 as a colorless oil (266 mg, 88%). Notably, the tert-butyldimethylsilyl group was fully intact under these conditions, and the received product 1 represented 100% selectivity in the removal of triphenylsilyl group in the presence of the tert-butyldimethylsilyl group. $^1$H NMR (300 MHz, CDCl$_3$) δ 4.01 (dt, J=2.4, 9.6 Hz, 1H), 3.90 (dt, J=4.5, 10.8 Hz, 1H), 3.85 (dt, J=5.1, 10.8 Hz, 1H), 3.68 (dd, J=2.1, 2.4 Hz, 1H), 2.63 (dq, J=3.3, 6.9 Hz, 1H), 1.98 (dddd, J=2.4, 5.4, 8.1, 14.1 Hz, 1H), 1.85 (dt, J=4.8, 9.3 Hz, 1H), 1.80 (dt, J=4.5, 9.3 Hz, 1H), 1.22 (d, J=6.6 Hz, 3H), 1.03 (d, J=7.2 Hz, 3H), 0.87 (s, 9H), 0.07 (s, 3H), 0.05 (s, 3H).

It was consistently observed that 2 of Examples 1 and 3 is UV-active under UV-light 254/365 nm while 1 lacks any UV-activity. The UV-activity is an advantage as it provides facile reaction monitoring without the need for special staining techniques. In addition, samples of 2 were stable at −20° C. for extended periods (months) without loss of UV-activity or desilylation of the triphenylsilyl and tert-butyldimethylsilyl groups.

Example 4. Exemplary Synthesis of Further Crystalline Compounds of the Present Technology

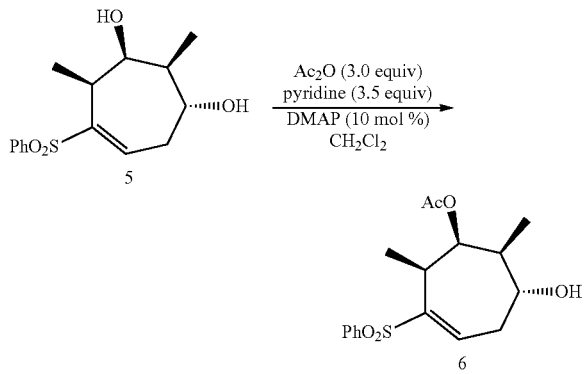

A 50 mL round bottom flask was charged with 5 (5.0 g, 12.18 mmol, 1 equiv), dichloromethane (30 mL), pyridine (3.43 mL, 42.62 mmol, 3.5 equiv), and 4-dimethylaminopyridine (150 mg, 1.218 mmol, 0.1 equiv). Acetic anhydride (3.45 mL, 36.54 mmol, 3.0 equiv) was added dropwise, and stirring was continued for 12 h. The organic phase was washed with 5% aqueous HCl (30 mL), washed with saturated aqueous NaHCO$_3$ (30 mL), dried with brine (30 mL), and with anhydrous Na$_2$SO$_4$. Filtration followed by concentration in vacuum afforded a yellow crystalline solid. Recrystallization from hexane-dichloromethane afforded 6 as pale yellow crystals (3.9 g, 95%). $^1$H NMR (300 MHz, CDCl$_3$) δ 7.82 (d, J=8.1 Hz, 2H), 7.59 (dt, J=1.5, 6.9 Hz, 1H), 7.50 (dt, J=1.5, 6.9 Hz, 2H), 7.16 (t, J=6.9 Hz, 1H), 5.27 (s, 1H), 4.95 (t, J=3.9 Hz, 1H), 3.74 (t, J=5.4 Hz, 1H), 2.88 (ddd, J=3.9, 7.2, 14.4 Hz, 1H), 2.75 (dd, J=6.6, 15.9 Hz, 1H), 2.61 (dt, J=7.2, 15.6 Hz, 1H), 2.00 (s, 3H), 1.13 (d, J=7.2 Hz, 3H), 1.05 (d, J=6.9 Hz, 3H).

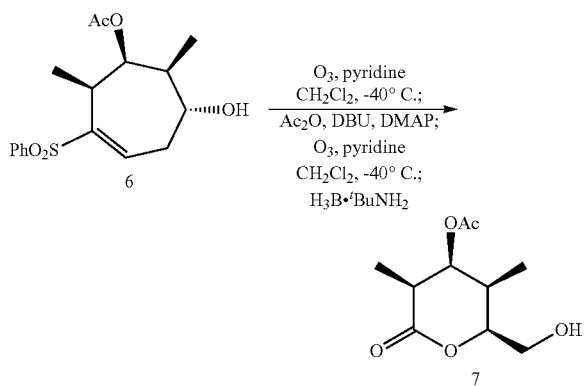

Figure 2:
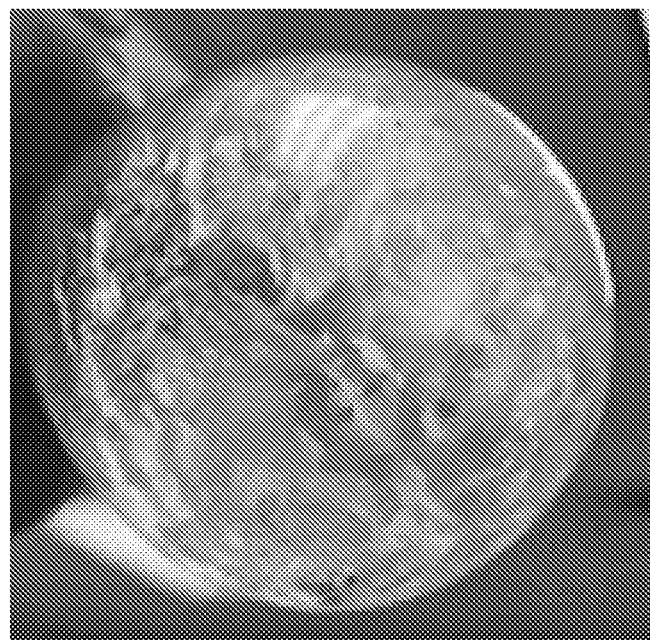
FIG. 2 provides a photograph of crystals of another embodiment of the present technology, according to the working examples.

To a 100 mL dry 3-neck flask was fit with a gas inlet adapter attached to a gas dispersion tube, a drying tube, and an outlet to 10% aqueous potassium iodide solution. The flask was charged with 6 (2.0 g, 5.92 mmol, 1 equiv; described above), pyridine (2.4 mL, 29.6 mmol, 5.0 equiv), and dry dichloromethane (60 mL). The resulting solution was cooled to −40° C., ozone was bubbled for 60 minutes, then purged with argon for 30 minutes. The solution was concentrated under vacuum, the resulting oil was dissolved in dichloromethane (15 mL), and acetic anhydride (2.8 mL, 29.6 mmol, 5.0 equiv) was added followed by DBU (1.8 mL, 11.84 mmol, 2.0 equiv). After 12 h, the yellow solution was cooled to −40° C., pyridine (2.4 mL, 29.6 mmol, 5.0 equiv) was added, and ozone was bubbled for 60 minutes, then purged with argon for 30 minutes. After cooling for 30 minutes at 5° C., H$_3$B·$^t$BuNH$_2$ (773 mg, 8.88 mmol, 1.5 equiv) was added, and stirring was continued for 30 minutes. The organic phase was washed with 5% aqueous HCl (30 mL), saturated aqueous NaHCO$_3$ (30 mL), dried with brine (30 mL), then with anhydrous sodium sulfate. The organic phase was filtered and concentrated under vacuum to give a crude brown oil. Purification over a short silica pad afforded alcohol 7 as pale yellow crystals (793 mg, 62%). $^1$H NMR (300 MHz, CDCl$_3$) δ 4.92 (dd, J=4.3, 5.2 Hz, 1H), 4.72 (dt, J=3.2, 4.8 Hz, 1H), 3.84-3.81 (2H, 3.82 (d, J=4.9 Hz, 1H), 3.82 (d, J=4.9 Hz, 1H)), 2.70 (dq, J=5.2, 6.6 Hz, 1H), 2.23-2.07 (4H, 2.15 (qdd, J=3.2, 4.3, 6.8 Hz, 1H, 1H, 2.07 (s, 3H)), 1.24 (d, J=7.2 Hz, 3H), 1.02 (d, J=6.9 Hz, 3H). FIG. 2 provides a photograph of the crystals of 7.

While certain embodiments have been illustrated and described, a person with ordinary skill in the art, after reading the foregoing specification, can effect changes, substitutions of equivalents and other types of alterations to the compounds of the present technology. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present technology may include, but is not limited to, the features and combinations of features recited in the following lettered paragraphs, it being understood that the following paragraphs should not be interpreted as limiting the scope of the claims as appended hereto or mandating that all such features must necessarily be included in such claims:

A. A compound of Formula I

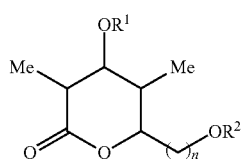

or a pharmaceutically acceptable salt and/or solvate thereof, wherein
  $R^1$ is H, trimethylsilyl (TMS), triethylsilyl (TES), tert-butyl-dimethylsilyl (TBS), triisopropylsilyl (TIPS), tert-butyl-diphenylsilyl (TBDPS), triphenylsilyl, dimethylphenylsilyl, methyldiphenylsilyl, acetyl (Ac), pivaloyl (Piv), trichloroacetyl, 2,2,2-trichloroethoxycarbonyl (Troc), benzyl, p-methoxybenzyl (PMB), 3-(phenylsulfonyl)propionyl, tosyl (Ts), or mesyl (Ms);
  $R^2$ is H, TMS, TES, TBS, TIPS, TBDPS, triphenylsilyl, dimethylphenylsilyl, methyldiphenylsilyl, Ac, Piv, trichloroacetyl, Troc, benzyl, PMB, 3-(phenylsulfonyl)propionyl, Ts, or Ms; and
  n is 1 or 2;
  provided that the compound of Formula I is not

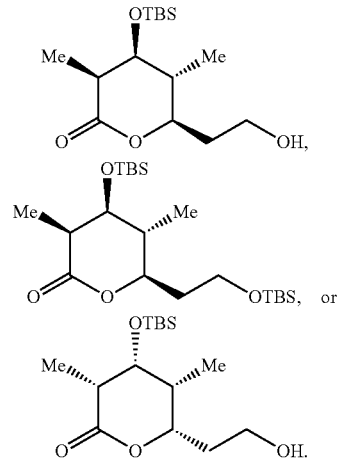

B. The compound of Paragraph A, wherein the compound of Formula I is not

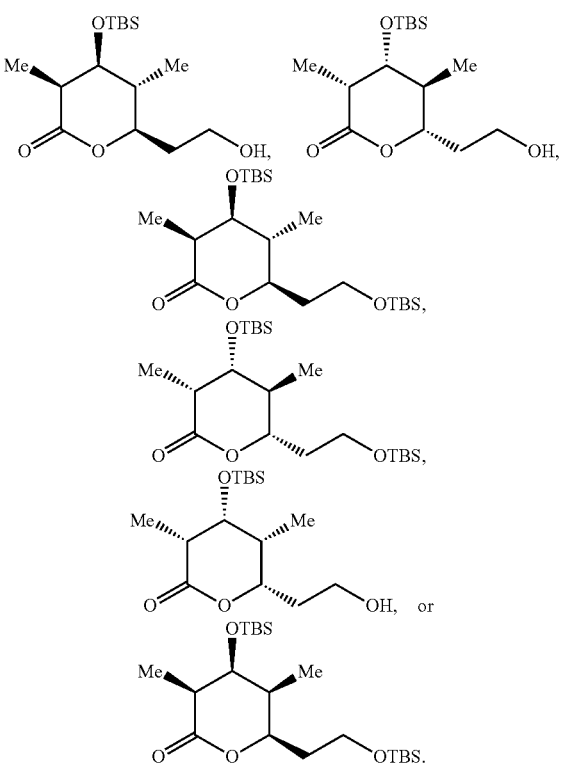

C. The compound of Paragraph A or Paragraph B, wherein $R^1$ is TBS or acetyl.

D. The compound of any one of Paragraphs A-C, wherein $R^2$ is triphenylsilyl.

E. The compound of any one of Paragraphs A-D, wherein the compound of Formula I is a crystalline solid.

F. The compound of any one of Paragraphs A-E, wherein the compound of Formula I is of Formula $I_1$ (I₁)

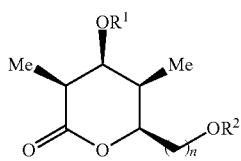

or a pharmaceutically acceptable salt and/or solvate thereof.

G. The compound of any one of Paragraphs A-E, wherein the compound of Formula I is of Formula I₂

(I₂)

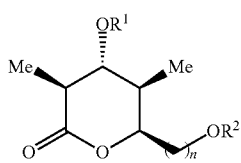

or a pharmaceutically acceptable salt and/or solvate thereof.

H. The compound of any one of Paragraphs A-E, wherein the compound of Formula I is of Formula I₃

(I₃)

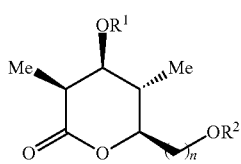

or a pharmaceutically acceptable salt and/or solvate thereof.

I. The compound of any one of Paragraphs A-E, wherein the compound of Formula I is of Formula I₄

(I₄)

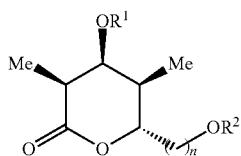

or a pharmaceutically acceptable salt and/or solvate thereof.

J. The compound of any one of Paragraphs A-E, wherein the compound of Formula I is of Formula I₅

(I₅)

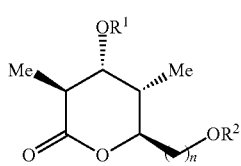

or a pharmaceutically acceptable salt and/or solvate thereof.

K. The compound of any one of Paragraphs A-E, wherein the compound of Formula I is of Formula I₆

(I₆)

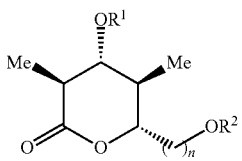

or a pharmaceutically acceptable salt and/or solvate thereof.

L. The compound of any one of Paragraphs A-E, wherein the compound of Formula I is of Formula I₇

(I₇)

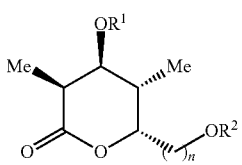

or a pharmaceutically acceptable salt and/or solvate thereof.

M. The compound of any one of Paragraphs A-E, wherein the compound of Formula I is of Formula I₈

(I₈)

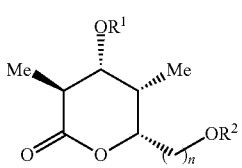

or a pharmaceutically acceptable salt and/or solvate thereof.

N. The compound of any one of Paragraphs A-E, wherein the compound of Formula I is of Formula I₉

(I₉)

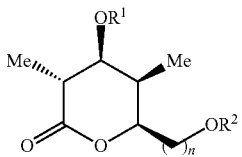

or a pharmaceutically acceptable salt and/or solvate thereof.

O. The compound of any one of Paragraphs A-E, wherein the compound of Formula I is of Formula I₁₀

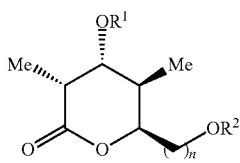

(I$_{10}$)

or a pharmaceutically acceptable salt and/or solvate thereof.

P. The compound of any one of Paragraphs A-E, wherein the compound of Formula I is of Formula I$_{ii}$

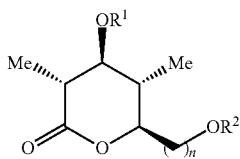

(I$_{11}$)

or a pharmaceutically acceptable salt and/or solvate thereof.

Q. The compound of any one of Paragraphs A-E, wherein the compound of Formula I is of Formula I$_{12}$

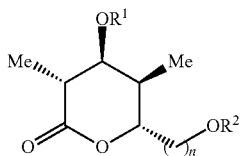

(I$_{12}$)

or a pharmaceutically acceptable salt and/or solvate thereof.

R. The compound of any one of Paragraphs A-E, wherein the compound of Formula I is of Formula I$_{13}$

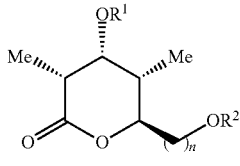

(I$_{13}$)

or a pharmaceutically acceptable salt and/or solvate thereof.

S. The compound of any one of Paragraphs A-E, wherein the compound of Formula I is of Formula I$_{14}$

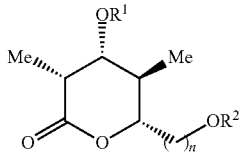

(I$_{14}$)

or a pharmaceutically acceptable salt and/or solvate thereof.

T. The compound of any one of Paragraphs A-E, wherein the compound of Formula I is of Formula I$_{15}$

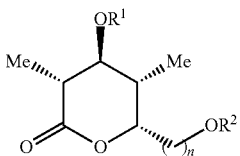

(I$_{15}$)

or a pharmaceutically acceptable salt and/or solvate thereof.

U. The compound of any one of Paragraphs A-E, wherein the compound of Formula I is of Formula I$_{16}$

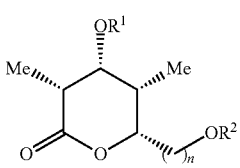

(I$_{16}$)

or a pharmaceutically acceptable salt and/or solvate thereof.

V. The compound of any one of Paragraphs A-U, wherein n is 1.

W. The compound of any one of Paragraphs A-U, wherein n is 2.

X. The compound of any one of Paragraphs A-U, wherein the compound of Formula I is

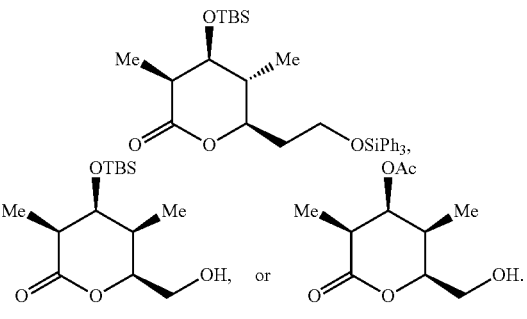

Other embodiments are set forth in the following claims, along with the full scope of equivalents to which such claims are entitled.

What is claimed is:

1. A compound of any one of Formulas I$_1$, I$_3$, and I$_{12}$-I$_{16}$:

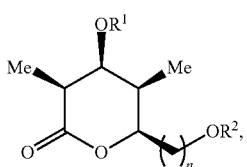

(I$_1$)

-continued

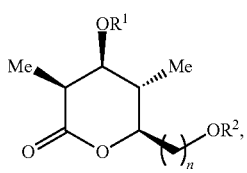
(I₃)

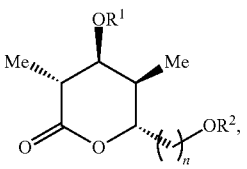
(I₁₂)

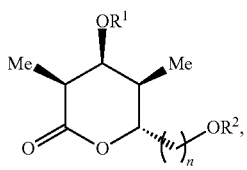
(I₄)

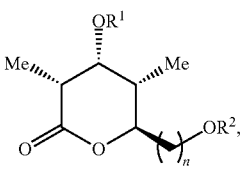
(I₁₃)

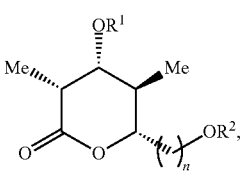
(I₁₄)

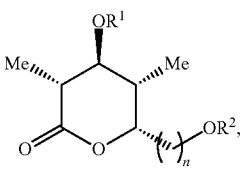
(I₁₅)

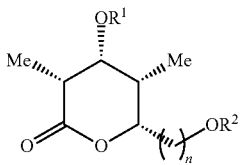
(I₁₆)

or a solvate thereof, wherein
R¹ is independently at each occurrence tert-butyl-dimethylsilyl;
R² is independently at each occurrence triphenylsilyl;
n is independently at each occurrence 1 or 2; and
wherein the compound is a crystalline solid.

2. The compound of claim 1, wherein the compound is of Formula I₁:

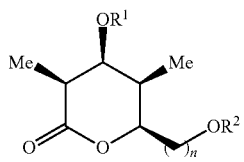
(I₁)

or a solvate thereof.

3. The compound of claim 1, wherein the compound is of Formula I₃:

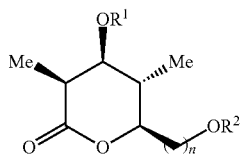
(I₃)

or a solvate thereof.

4. The compound of claim 1, wherein the compound is of Formula I₁₂:

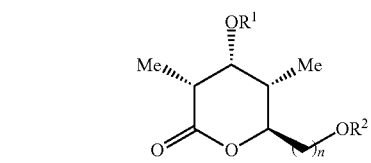
(I₁₂)

or a solvate thereof.

5. The compound of claim 1, wherein the compound is of Formula I₁₃:

(I₁₃)

or a solvate thereof.

6. The compound of claim 1, wherein the compound is of Formula $I_{14}$:
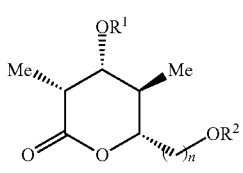
$(I_{14})$
or a solvate thereof.
7. The compound of claim 1, wherein the compound is of Formula $I_{15}$:
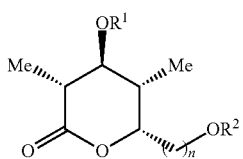
$(I_{15})$
or a solvate thereof.
8. The compound of claim 1, wherein the compound is of Formula $I_{16}$:
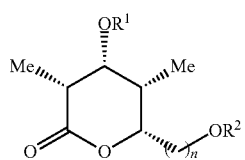
$(I_{16})$
or a solvate thereof.
9. The compound of claim 1, wherein the compound is:
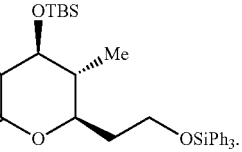
* * * * *

UNITED STATES PATENT AND TRADEMARK OFFICE
CERTIFICATE OF CORRECTION

PATENT NO. : 10,851,121 B2
APPLICATION NO. : 16/467892
DATED : December 1, 2020
INVENTOR(S) : Noshi et al.

Page 1 of 1

It is certified that error appears in the above-identified patent and that said Letters Patent is hereby corrected as shown below:

In the Claims

In Claim 1, Column 35, Lines 17-23:
Formula ($I_4$) should be removed.

Signed and Sealed this
Second Day of March, 2021

Drew Hirshfeld
*Performing the Functions and Duties of the*
*Under Secretary of Commerce for Intellectual Property and*
*Director of the United States Patent and Trademark Office*